US011833353B2

(12) United States Patent
Wilder et al.

(10) Patent No.: US 11,833,353 B2
(45) Date of Patent: Dec. 5, 2023

(54) ELECTRICAL ISOLATION OF NEUROSTIMULATION CIRCUITRY FROM NEURORECORDING CIRCUITRY

(71) Applicant: VERITAS IP, LLC, Salt Lake City, UT (US)

(72) Inventors: Andrew Miller Wilder, Salt Lake City, UT (US); Scott Darold Hiatt, South Jordan, UT (US); Steven John Barrus, North Salt Lake, UT (US); Cliff C. Nixon, Phoenix, AZ (US)

(73) Assignee: Veritas IP, LLC, Salt Lake City, UT (US)

( * ) Notice: Subject to any disclaimer, the term of this patent is extended or adjusted under 35 U.S.C. 154(b) by 322 days.

(21) Appl. No.: 17/315,160

(22) Filed: May 7, 2021

(65) Prior Publication Data

US 2021/0346700 A1 Nov. 11, 2021

Related U.S. Application Data

(60) Provisional application No. 63/022,384, filed on May 8, 2020.

(51) Int. Cl.
*A61N 1/02* (2006.01)
*A61N 1/36* (2006.01)
*A61B 5/00* (2006.01)
*G06F 3/01* (2006.01)
*A61N 1/08* (2006.01)

(52) U.S. Cl.
CPC ........ *A61N 1/36128* (2013.01); *A61B 5/7217* (2013.01); *A61N 1/025* (2013.01); *G06F 3/015* (2013.01); *A61N 2001/083* (2013.01)

(58) Field of Classification Search
CPC ............... A61N 1/36128; A61N 1/025; A61N 2001/083; A61N 1/36064; A61N 1/36071; A61N 1/36103; A61N 1/36185; A61N 1/36139; A61N 1/37235; A61N 1/3787; A61B 5/301; A61B 5/7217; A61B 5/686; A61B 5/0538; A61B 5/30; A61B 5/318; A61B 5/369; A61B 5/389; G06F 3/015;
(Continued)

(56) References Cited

U.S. PATENT DOCUMENTS

2018/0092565 A1 * 4/2018 Lee .................. A61B 5/369

* cited by examiner

*Primary Examiner* — Carl H Layno
*Assistant Examiner* — Anh-Khoa N Dinh
(74) *Attorney, Agent, or Firm* — PCFB, LLC; Jared L. Cherry

(57) ABSTRACT

Various embodiments of an interface control subsystem may be used between an electrode terminal and a recording terminal of a neurostimulation and neurorecording system. The interface control subsystem may operate in three modes. In a disable mode, a first transistor and a second transistor disposed between the electrode terminal and the recording terminal may operate in a cutoff region and generate a high impedance. In an active mode, the first transistor and the second transistor may operate in a saturation region and generate a low impedance. In a stimulation mode, the first transistor and the second transistor operate in a triode region and generate an impedance between the high impedance of the disable mode and the low impedance of the active mode. The interface control subsystem may further limit voltage at the recording terminal in response to a detected overvoltage condition.

23 Claims, 12 Drawing Sheets

(58) Field of Classification Search
CPC .... G06F 2218/12; G16H 50/50; G01R 27/04; H01B 1/22
See application file for complete search history.

ELECTRICAL ISOLATION OF NEUROSTIMULATION CIRCUITRY FROM NEURORECORDING CIRCUITRY

RELATED APPLICATIONS

This application claims priority to U.S. Provisional Application Patent Application No. 63/022,384, filed on May 8, 2020.

FEDERALLY SPONSORED RESEARCH OR DEVELOPMENT

This invention was made with U.S. Government support under contract no. W912CG-19-C-0004 awarded by the Defense Advanced Research Projects Agency. The U.S. Government may have certain rights in this invention.

TECHNICAL FIELD

This disclosure relates to a biological stimulator and recorder. More particularly, but not exclusively, the present disclosure relates to an application-specific integrated circuit (ASIC) that may be used to record biopotential signals (e.g., electroencephalogram (EEG), electromyogram (EMG), neural action potentials, electrocorticography (ECoG), electrocardiogram (ECG/EKG), etc.) and to selectively stimulate excitable tissue (e.g., neurons, nerves, cortical tissue, muscles, etc.) for neuromodulation, neuro-prosthetic and neuroscience applications.

DETAILED DESCRIPTION OF PREFERRED EMBODIMENTS

Figure 1:
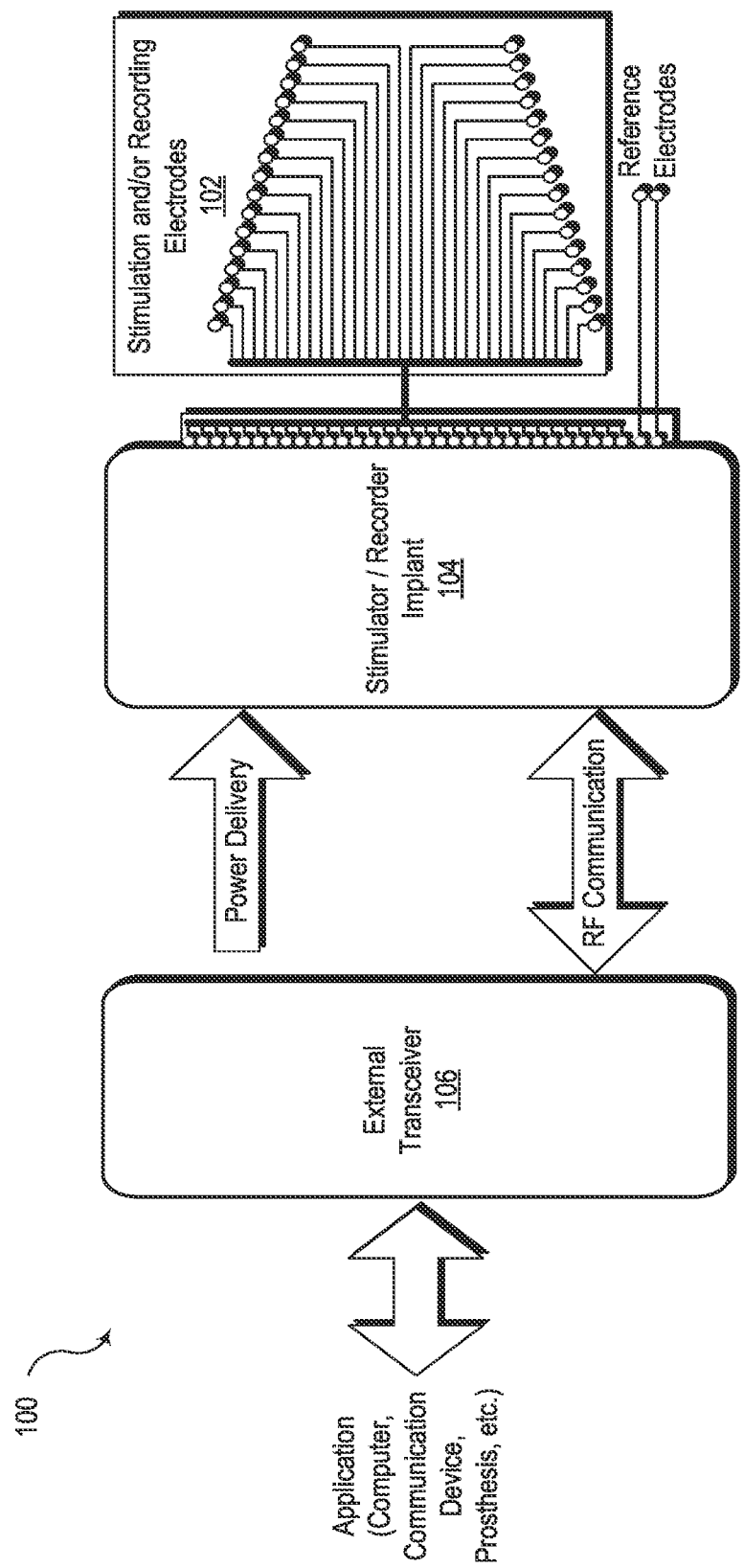
FIG. 1 illustrates a block diagram of an implanted biological stimulator and recorder system consistent with embodiments of the present disclosure.

Disclosed herein are various systems and methods for neurological stimulators and recorders. In various embodiments, the systems disclosed herein may be implanted in patients for various applications, such as interfacing with a computer, a communication device, a prosthesis, or other device. In other embodiments, the systems and methods disclosed herein may be used in neuroscience research applications or for clinical therapies.

Stimulation therapy may be used to treat a variety of conditions, such as epilepsy, depression, pain, cognitive function, restoration of motor function and restoration of sensation from damaged or amputated limbs. Stimulation therapy may be practiced by injecting a source current into neural tissue from one electrode and sinking that current out of the tissue using another electrode. Often, after a first stimulation pulse is delivered, a second stimulation pulse is delivered in the opposite direction (a sink electrode becomes the source electrode and vice versa) through the tissue. This approach, which is commonly referred to as balancing the charge, removes electrical charge from the tissue and prevents tissue damage. Recording, or sensing, neural pathways for electrical activity before and after stimulation may be used as a feedback mechanism in stimulation therapy.

Neurostimulation circuits may operate at a voltage that is relatively high in comparison to recording circuits that may also be used in stimulation therapy and other applications. For example, a neurostimulation circuit may use signals of 30 Volts to stimulate neural tissue. Recording or sensing circuits operate at a lower voltage (e.g., 5 Volts or less), and signals of interest may be as small as 1 uV. The large difference between stimulation and recording voltages presents challenges that may be addressed using various teachings in the present disclosure.

The inventors of the present disclosure have recognized that various advantages may be achieved by introducing an interface between the stimulation and recording elements, such that stimulation and recording elements may be included in the same system. An interface consistent with the present disclosure may allow a recording circuit to be optimized to receive low voltage signals and may present a low impedance and low noise path to the recording circuit when stimulation signals are not present. Further, when stimulation signals are present, the interface may provide high impedance to block current and voltage from entering the recording circuitry, thus allowing the recording circuitry to be optimized to receive low-voltage signals while protecting the recording circuitry from damage from the high voltage associated with stimulation.

In various embodiments, an interface consistent with the present disclosure may isolate a recording or sensing circuit from a stimulation circuit while the stimulation circuit is active and may also isolate the recording circuit based on an overvoltage condition. An overvoltage condition may result if, for example, an electrode is being recorded while another circuit is applying a stimulation pulse, and the stimulation current finds its way to the recording electrode. In such a case, the recording circuitry may be active, and as such, the interface may limit the voltage to protect the recording circuitry.

FIG. 1 illustrates a block diagram of a stimulation and recording system 100 consistent with embodiments of the present disclosure. An application (not shown), such as a computer or prosthetic device, may be controlled using a user's biopotentials. A stimulator/recorder implant 104 may collect biopotential signals. Biopotential signals are electrical differences between one or more electrodes. Such signals may be used to enable the patient to control the prosthetic device.

The stimulation and recording system 100 may include an external transceiver 106. The external transceiver may provide power to the stimulator/recorder implant 104. Further, the stimulator/recorder implant 104 and the external transceiver 106 may use radio frequency (RF) communication to exchange information. For example, stimulator/recorder implant 104 may transmit a recorded signal to the external transceiver 106 via RF communication, and the external transceiver 106 may transmit signals that are used to control stimulation of excitable tissues. The stimulator/recorder implant 104 and/or the external transceiver 106 may include circuitry and a processor to control an application, such as a prosthetic device.

Stimulation and/or recording electrodes 102 may be embodied in a variety of ways and using various technologies that collect biopotential signals from a patient and/or stimulate excitable tissues. Electrodes 102 may be arranged or configured in leads or sensors. Leads are structures that contain one or more electrodes or sensors that are individually placed or placed in conjunction with other leads.

Figure 2A:
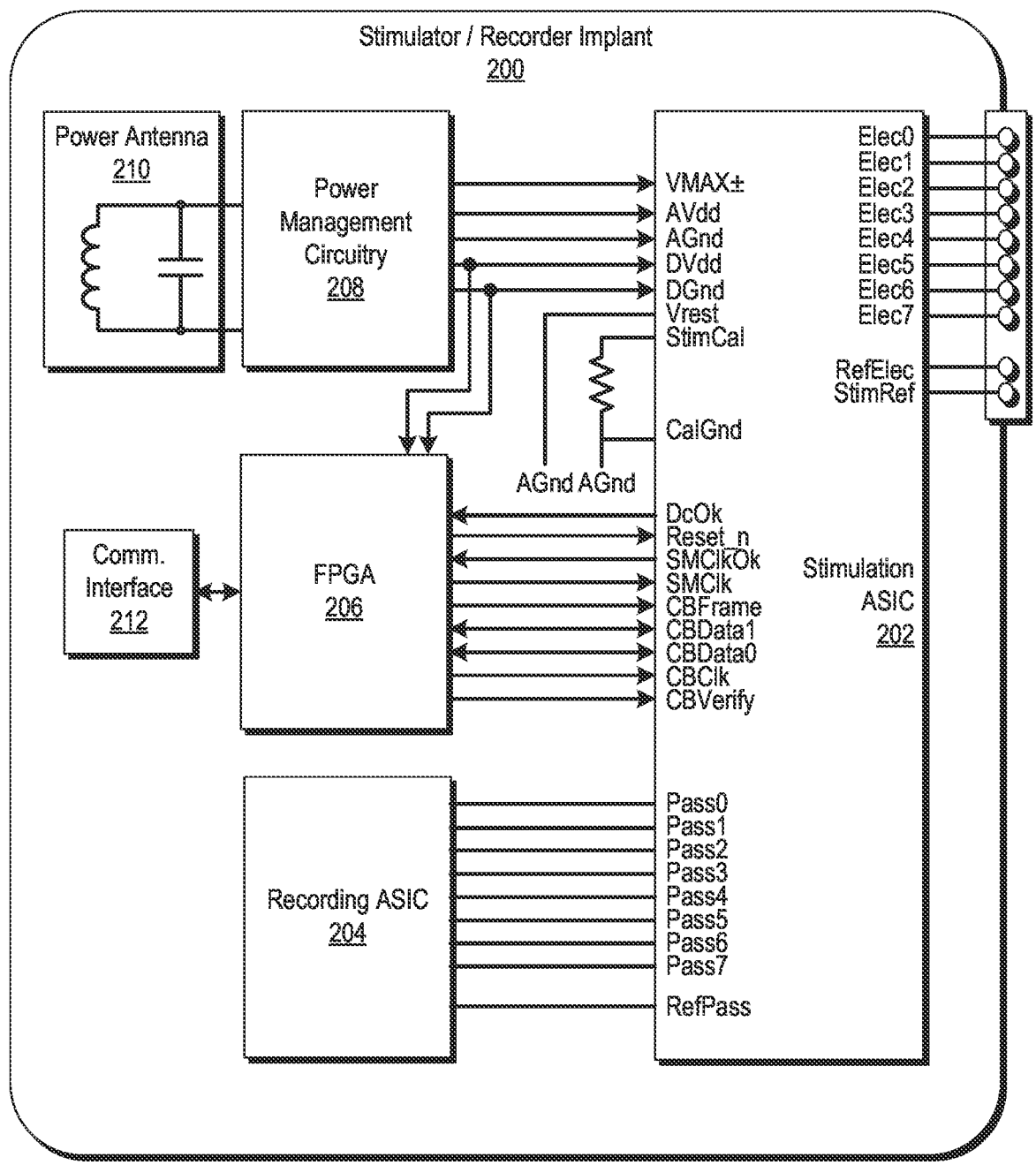
FIG. 2A illustrates a block diagram of a stimulator/recorder implant consistent with embodiments of the present disclosure.

FIG. 2A illustrates a block diagram of a stimulator/recorder implant 200 consistent with embodiments of the present disclosure. Stimulator/recorder implant 200 comprises a stimulation ASIC 202, a recording ASIC 204, a field-programmable gate array ("FPGA") 206, power management circuitry 208, and a power antenna 210. FPGA 206 may be used to process information from other components in stimulator/recorder implant 200. Further, FPGA 206 may be used to process communications with an external transceiver via communication interface 212. In various embodiments, communication interface 212 may use wireless communication technologies to transmit data. Wireless communication may allow for communication with an external transceiver while the stimulator/recorder implant 200 is implanted in a patient. In one specific embodiment, communication interface 212 may be embodied using the systems disclosed in U.S. patent Ser. No. 15/870,362, filed Jan. 12, 2018, and titled "Sensor System," which is incorporated herein by reference.

In various embodiments, stimulation ASIC 202 may provide a plurality of independently programmable current sources, each of which may provide current stimulation through a channel. Further, various embodiments may also provide a plurality of channels to record biopotential signals using recording ASIC 204. The stimulation and record channels may connect to an implanted electrode array (e.g., the stimulation and/or recording electrodes 102 illustrated in FIG. 1). Power antenna 210 may comprise an inductor to inductively couple to an external power supply. Power management circuitry 208 may render the power received from power antenna 210 suitable for use by other components in stimulator/recorder implant 200.

In the illustrated embodiment, stimulation ASIC 202 includes eight independently programmable stimulation channels, which are labeled Elec0 through Elec7. Each channel may include constant current output drivers to source and sink current and low noise injection to allow for amplification of biopotential signals. In one specific embodiment, the biopotential signal levels may range from about 10 uV to 10 mV. In some embodiments, an amplification subsystem may be used to amplify signals provided to stimulation ASIC 202. In some embodiments, stimulation ASIC 202 allows for routing of appropriate excitation signals for electrode impedance measurement (e.g., using the impedance matrix illustrated in FIG. 10), using internal circuits for calibration for channel current source elements, as well as methods for detecting internal faults that may lead to undesirable DC electrode currents (e.g., the circuit illustrated in FIG. 9). Stimulation ASIC 202 may include digital control logic for the control of each channel and system-level logic that provides control of ASIC functions common to all channels.

Signals from stimulation ASIC 202 may be passed to recording ASIC 204 through channels identified as Pass0 through Pass7, which may correspond to channels identified as Elec0 through Elec 7. Similarly, a Stim Ref signal may be passed to the recording ASIC 204 through the channel RefPass. An interface consistent with the present disclosure may be incorporated into stimulation ASIC 202 or recording ASIC 204. The interface disposed between the channels identified as Elec0-Elec7 and the channels identified as Pass0-Pass7 may isolate a recording or sensing circuit from a stimulation circuit while the stimulation circuit is active and may also isolate the recording circuit based on an overvoltage condition. An overvoltage condition may result if, for example, an electrode is being recorded while another circuit is applying a stimulation pulse, and the stimulation current finds its way to the recording electrode. In such a case, the recording circuitry may be active, and as such, the interface may limit the voltage to protect the recording circuitry.

Figure 11:
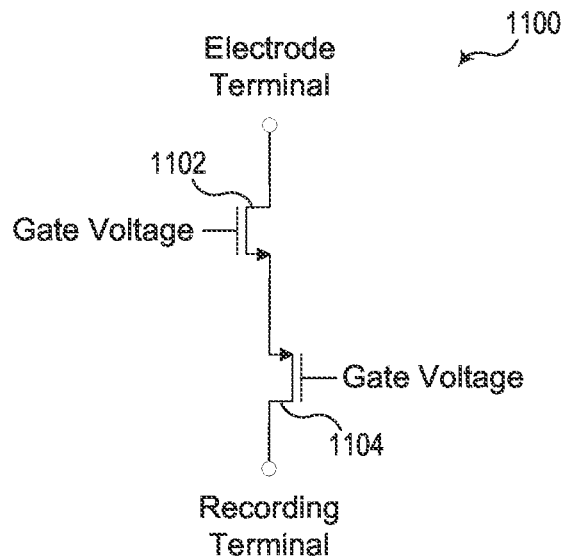
FIG. 11 illustrates a circuit diagram of an interface between a recording circuit and a stimulation circuit consistent with embodiments of the present disclosure.
Figure 12:
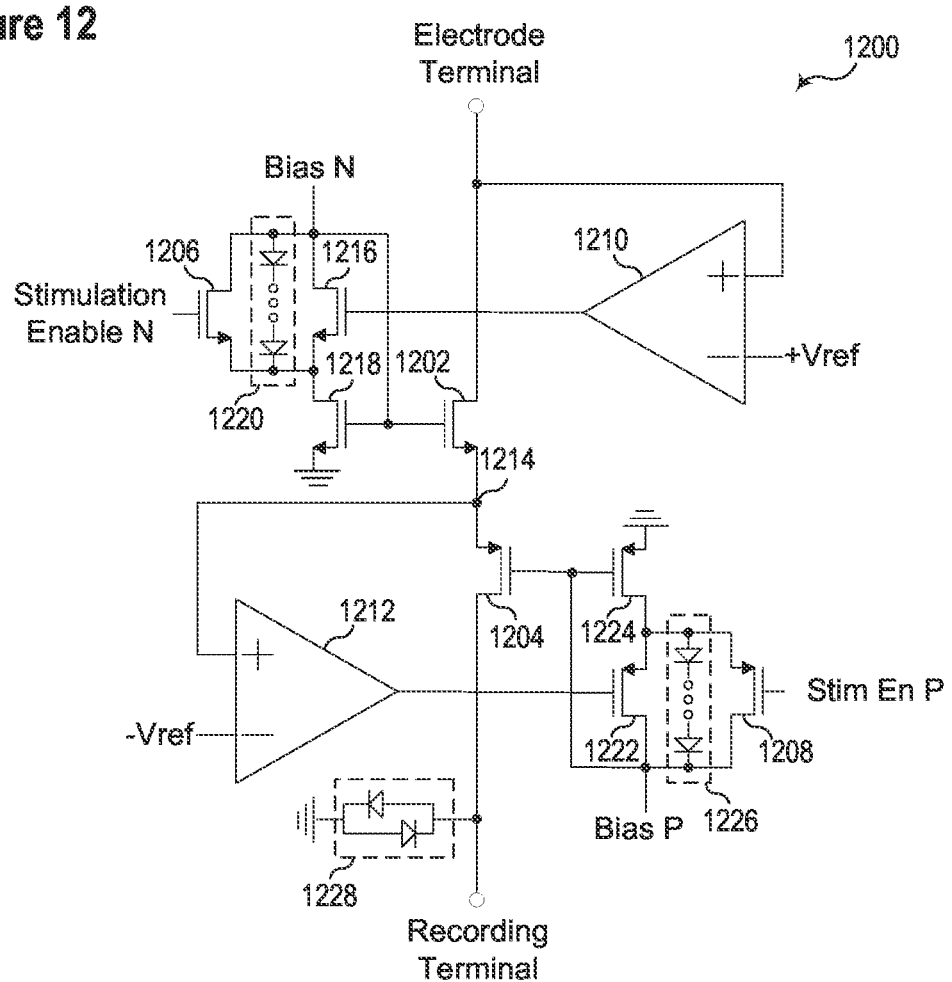
FIG. 12 illustrates a circuit diagram of an electrode and recording interface control circuit consistent with embodiments of the present disclosure.

In various embodiments, the interface between the channels identified as Elec0 through Elec 7 and Pass0 through Pass7 may be embodied using the specific interface circuit configurations illustrated in FIG. 11 and/or FIG. 12. For example, the "electrode terminal" illustrated in FIG. 11 and/or FIG. 12 may be in electrical communication with Elec0, and the "recording terminal" illustrated in FIG. 11 and/or FIG. 12 may be in electrical communication with Pass0. A separate interface may be provided for each channel of stimulator/recorder implant 200.

Stimulation ASIC 202 may be designed to minimize size. Small size may facilitate implantation and use in a variety of types of applications. Accordingly, external components may be integrated into stimulator/recorder implant 200 or eliminated to reduce size.

Figure 2B:
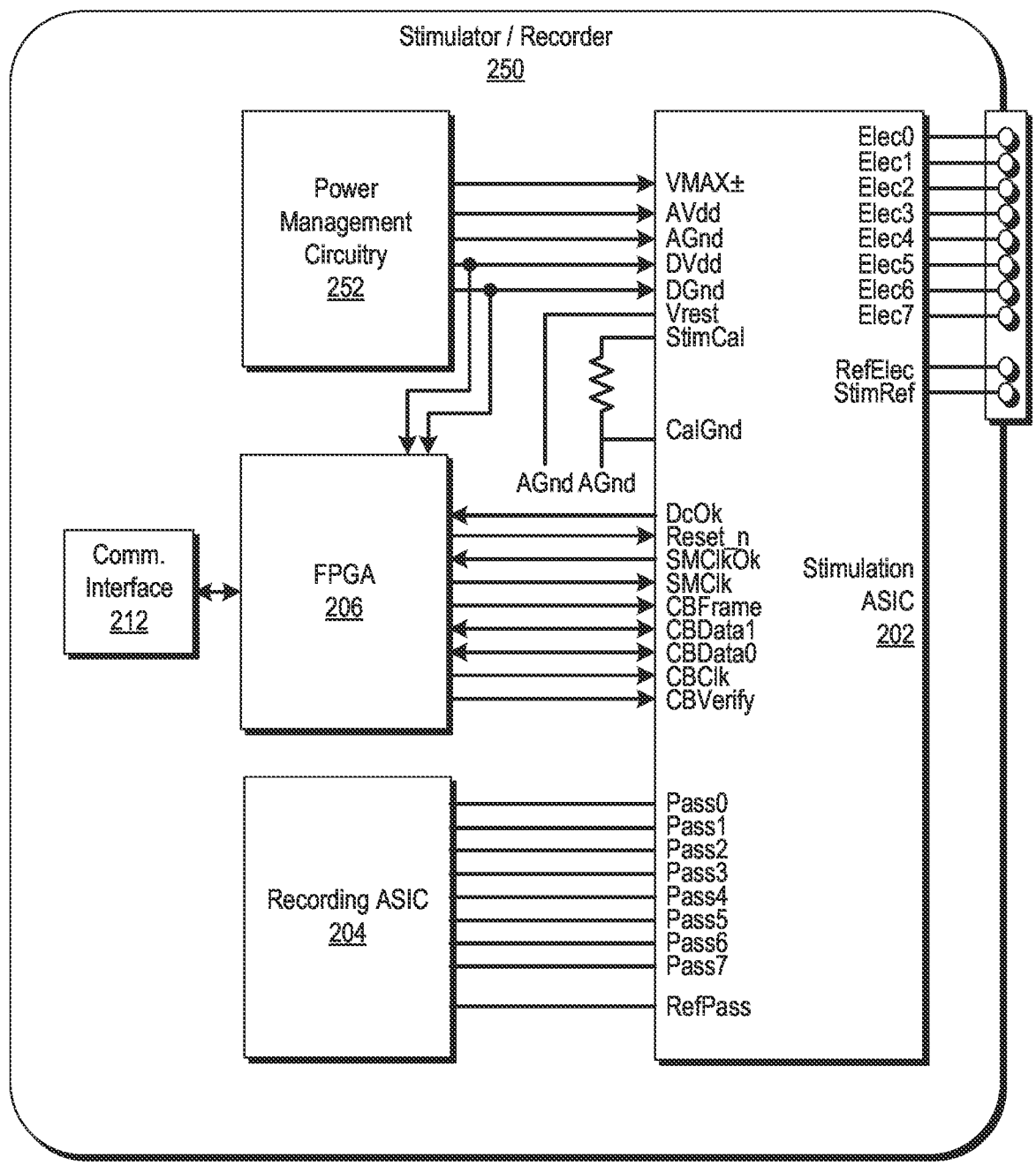
FIG. 2B illustrates a block diagram of a stimulator/recorder non-implantable module consistent with embodiments of the present disclosure.

FIG. 2B illustrates a block diagram of a stimulator/recorder module 250 that is not implantable consistent with embodiments of the present disclosure. Module 250 may operate similarly to stimulator/recorder implant 200 but may operate without implantation. Accordingly, power management circuitry 252 may interface directly with a power supply, rather than receiving power wirelessly.

Figure 3:
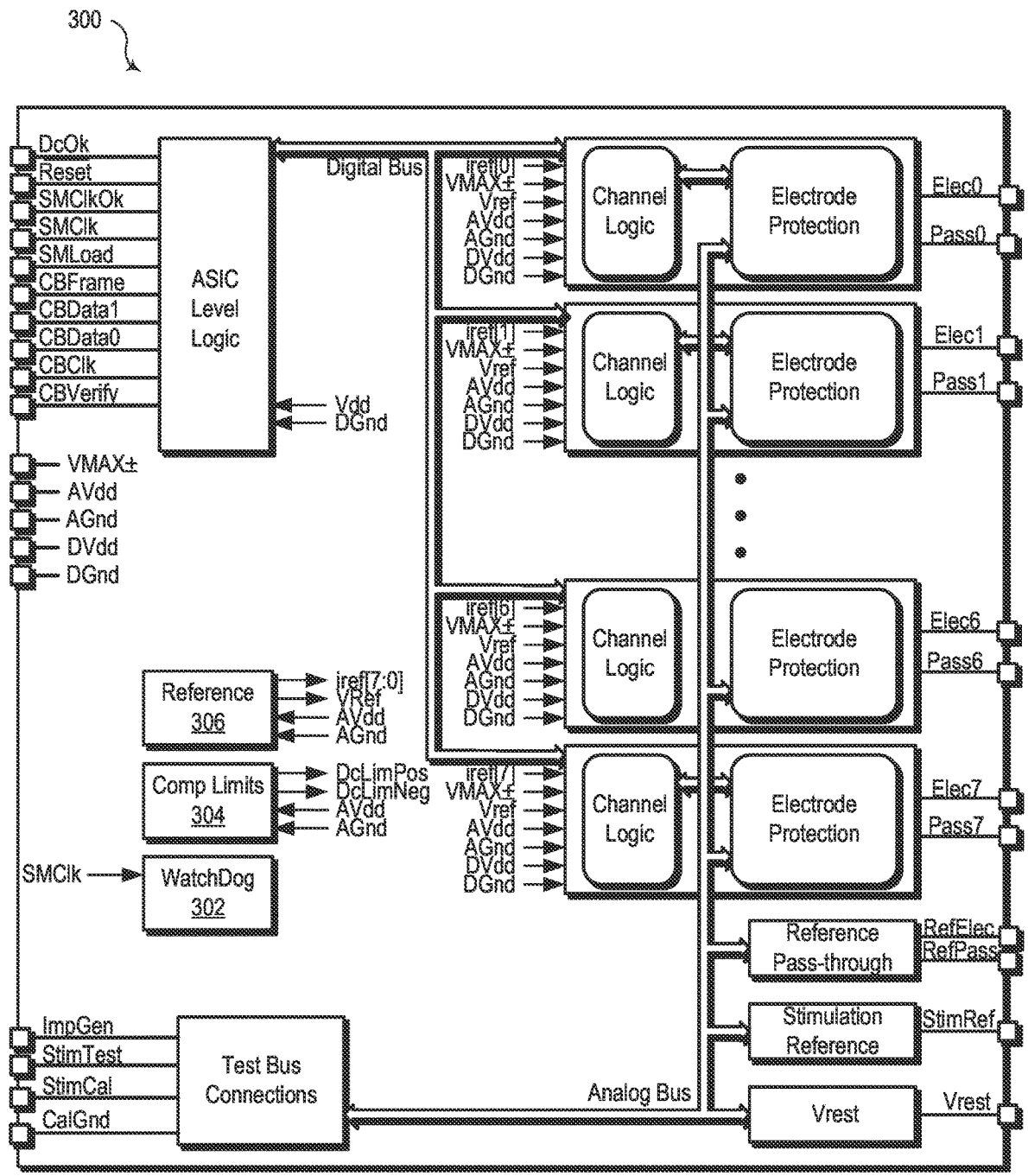
FIG. 3 illustrates a block diagram showing certain input and output signals of an ASIC to isolate recording circuitry and stimulation circuitry consistent with embodiments of the present disclosure.

FIG. 3 illustrates a block diagram showing certain input and output signals of an ASIC 300 to isolate recording circuitry and stimulation circuitry consistent with embodiments of the present disclosure. In the illustrated embodiment, each of the eight channels includes an electrode protection block (e.g., the generic protection block illustrated in FIG. 7 or the specific circuits illustrated FIG. 11 and FIG. 12) and other features. The protection block may isolate a recording or sensing circuit from a stimulation circuit while the stimulation circuit is active and may also isolate the recording circuit based on an overvoltage condition. The protection block may ensure proper operation of the system during internal stimulation testing and calibration connections (e.g., such as the testing circuit illustrated in FIG. 10) and electrode impedance test signal routing to each electrode.

WatchDog block 302 may monitor the system clock signal (SMClk) and output a reset signal if the clock stops. Since this is a fault detection function, the WatchDog 302 block may operate autonomously from other elements in ASIC 300. In one embodiment, the WatchDog block 302 may output the reset signal within 1 ms from the time that the system clock stops. The reset signal may end all stimulation outputs from the ASIC 300 and may disconnect the stimulation circuits from the electrode connections in various embodiments.

Comparator limits block 304 may generate reference signals for use by comparators in ASIC 300. In the illustrated embodiment, comparator limits block 304 generates the signals DcLimPos and DcLimNeg. The signals DcLimPos and DcLimNeg may be used to check for unexpected voltages on any individual electrode due to circuit damage or other fault.

A reference block 306 may provide reference currents for each stimulation channel, iref[7:0], and a reference voltage, VRef. In some embodiments, an on-chip adjustable reference resistor may be used to provide an accurate current reference. Further, reference block 306 may provide bias currents for analog circuitry in ASIC 300.

Figure 4:
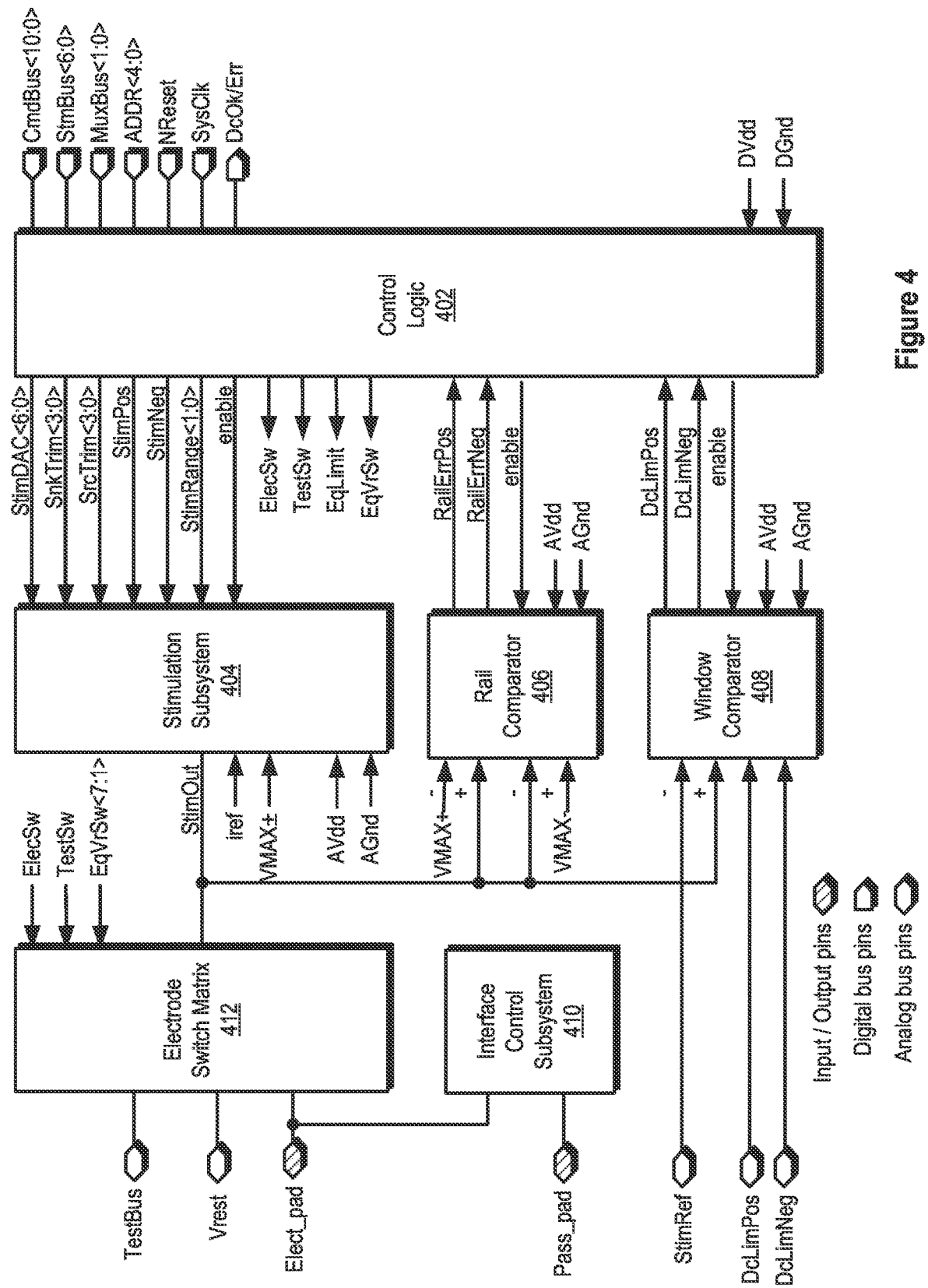
FIG. 4 illustrates a block diagram of an individual channel of control logic and other analog circuitry consistent with the present disclosure.
Figure 5:
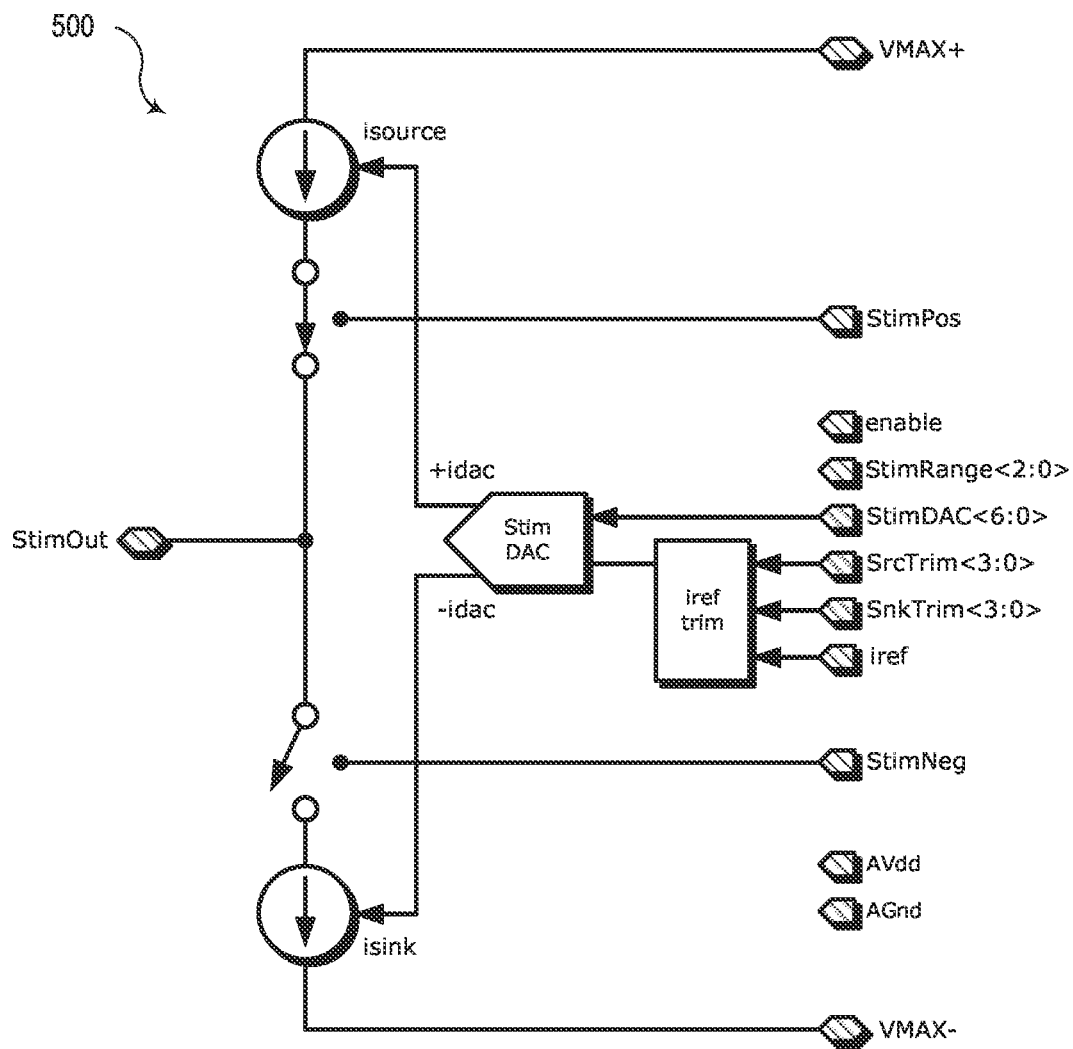
FIG. 5 illustrates a block diagram of a stimulation subsystem with individual channel calibration consistent with the present disclosure.

FIG. 4 illustrates a block diagram of a control logic system consistent with the present disclosure. Control logic 402 may provide signals to a stimulation subsystem 404. The signals may be used to generate an electrical signal, StimOut, that is passed to an electrode (not shown) and used to stimulate excitable tissues. One specific embodiment of circuitry that may be included in an embodiment of stimulation subsystem 404 is illustrated in FIG. 5 and described in greater detail below. As one of skill in the art will appreciate, the embodiment illustrated in FIG. 5 is merely representative of a variety of possible embodiments of stimulation subsystem 404.

A rail comparator 406 and a window comparator 408 may be used to ensure that signals remain within specific ranges. A rail comparator 406 may operate during a stimulation event and may assert when the StimOut output is within a threshold value of near a positive or negative voltage rail used to drive the stimulation currents. In one specific embodiment, the rail comparator 406 may signal a fault when the StimOut output is within 700 mV of these voltage rails. A window comparator 408 may determine whether a voltage on an electrode is within a voltage window established by a maximum threshold and a minimum threshold, to verify that when the stimulation circuit is not active, the resting potential of the electrode is within the expected safety range.

An interface control subsystem 410 may isolate stimulation and recording terminals. An Elect_pad signal may be connected to an electrode (not shown) that may be used for both stimulation and recording, and a Pass_pad signal may be connected to a recording system (e.g., a recording ASIC, such as recording ASIC 204 in FIG. 2A or FIG. 2B). Interface control subsystem 410 may present a low impedance and low noise path to the recording circuit when stimulation signals are not present. In contrast, when stimulation signals are present, the interface control subsystem 410 may provide high impedance to isolate recording circuitry from stimulation circuitry, and thus allow the recording circuitry to be optimized to receive low-voltage signals while protecting the recording circuitry from damage from the high voltage associated with stimulation. Two specific embodiments of interface control subsystem 410 are illustrated in FIG. 11 and FIG. 12. As one of skill in the art will appreciate, the embodiments illustrated in FIG. 11 and FIG. 12 are merely representative of a variety of possible embodiments of interface control subsystem 410.

Figure 6:
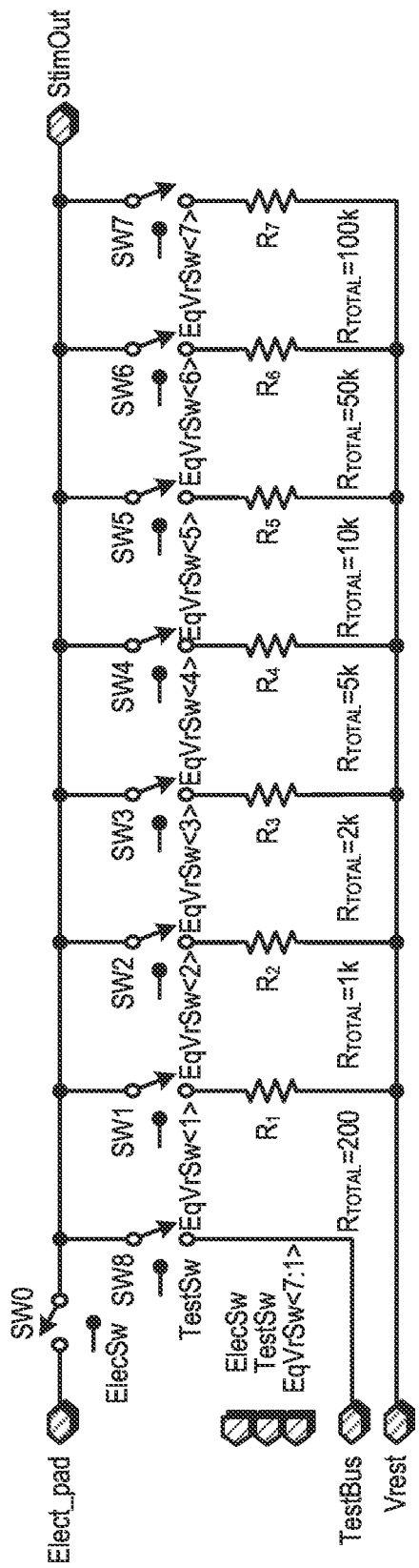
FIG. 6 illustrates a switch matrix with a selection of application specific resistors for post-stimulation exhausting of residual charge after stimulating excitable tissue consistent with the present disclosure.

An electrode switch matrix 412 may provide a variety of impedances that may be selectively connected to an electrode in electrical communication with the Elect_pad input/output pin. A specific impedance may be selected to match the amplitude of the stimulation currents and desired recovery time. A recovery time refers to the time required between stimulation pulses or between a simulation pulse and desired recording. A more intense stimulation pulse may be associated with a longer recovery time in comparison to a less intense stimulation pulse. Still further, electrode switch matrix 412 may allow an electrode to be tested and calibrated. One specific embodiment of electrode switch matrix 412 is illustrated in FIG. 6 and described in greater detail below. As one of skill in the art will appreciate, the embodiment illustrated in FIG. 6 is merely representative of a variety of possible embodiments of electrode switch matrix 412.

FIG. 5 illustrates a block diagram of a stimulation subsystem 500 consistent with the present disclosure. The stimulation subsystem 500 both sources and sinks accurate current pulses to the StimOut output. An output may be used as an independent stimulation source or coupled with another channel to act as a bipolar pair. Each current pulse may be delivered through its respective electrode to the targeted tissue. Both source and sink current sources may include independent trims, SrcTrim<3:0> and SnkTrim<3:0>, to achieve a specified accuracy for medical devices. In the illustrated embodiment, a common 7-bit, StimDAC<6:0>, channel current digital-to-analog ("DAC") converter sets both a source and a sink current level along with the selectable full-scale range command, StimRange<1:0>. StimDAC, SrcTrim, and SnkTrim controls may be updated in real-time or near real-time for current waveform synthesis.

FIG. 6 illustrates a switch matrix that may be used in one or more electrodes for exhausting residual charge, through a variety of resistors selected based on specific electrode impedance and desired recovery time, after stimulating excitable tissue consistent with the present disclosure. The switch matrix also allows the StimOut to be selectively connected to a Testing and Calibration Bus (TestBus), or the Elect_pad, or Vrest signal. As illustrated, SW0 may be closed to connect the Elect_pad to the StimOut output, SW1-SW7 may be closed to connect the Vrest signal to the StimOut output through various resistance values to accomplish the exhausting function, and SW8 may be used to connect the StimOut directly to the TestBus.

Figure 7:
FIG. 7 illustrates an electrode protection subsystem consistent with the present disclosure.

FIG. 7 illustrates an electrode protection subsystem 700 consistent with the present disclosure. Each channel may include a series clamp circuit to protect a recording ASIC from the voltages caused by stimulation outputs. In the illustrated embodiment, the electrode protection subsystem 700 clamps the voltage to less than +/−400 mV. In one specific embodiment, the impedance for this path is less than 200 Ohms when not clamping voltage in excess of the protection system limits. Specific embodiments of circuitry for implementing an electrode protection are illustrated and described in connection with FIG. 11 and FIG. 12.

Figure 8:
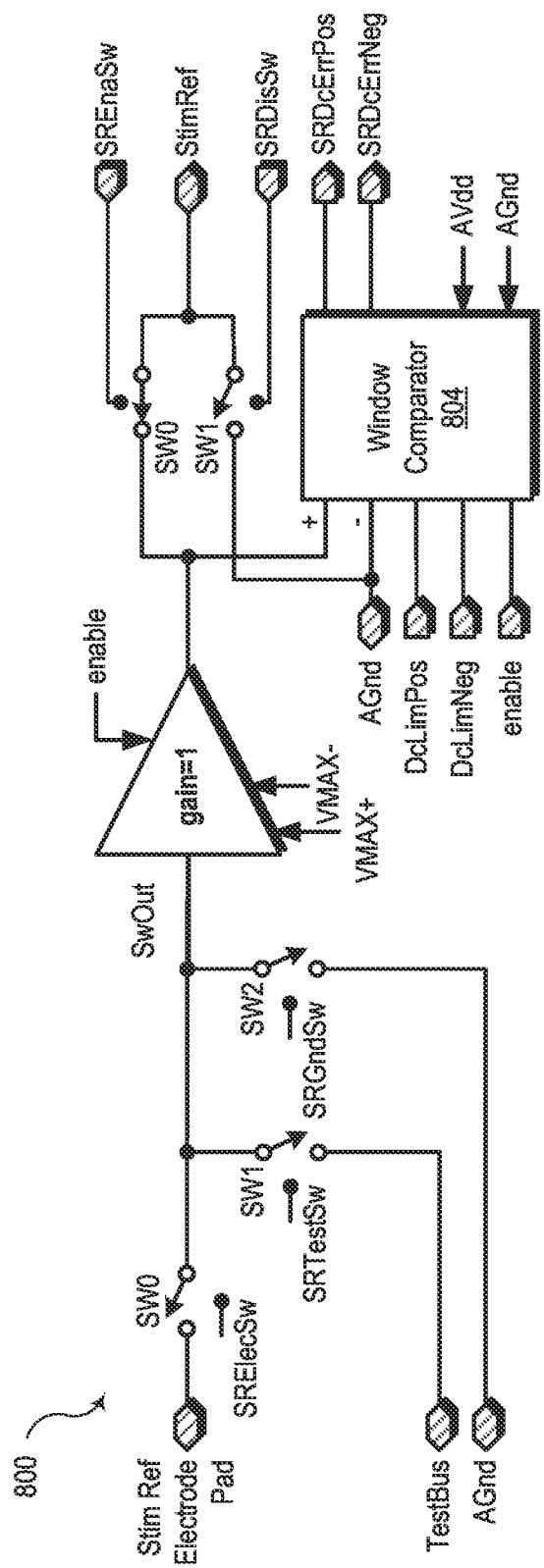
FIG. 8 illustrates a block diagram of a DC limit test circuit to allow detection of unexpected stimulation or unexpected leakage currents consistent with the present disclosure.

FIG. 8 illustrates a block diagram of a stimulation reference subsystem 800 consistent with the present disclosure. The Stim Ref pin may be used as the common low-level reference for a window comparator across all channels. The TestBus pin may be connected to a stimulation reference electrode switch matrix, such as the switch matrix described in connection with FIG. 6. The AGnd pin may be connected to the circuit ground. These signals may be buffered by a unity gain amplifier and applied to the input of a window comparator 804.

In the illustrated embodiment, window comparator 408 generates a first signal, SRDcErrPos, when the DC voltage is above the maximum threshold and generates a second signal, SRDcErrNeg, when the DC voltage on the electrode is the minimum threshold. The illustrated embodiment allows threshold voltages to be independently programmable and optimize thresholds for rapid detection of errors on different electrode compositions.

Figure 9:
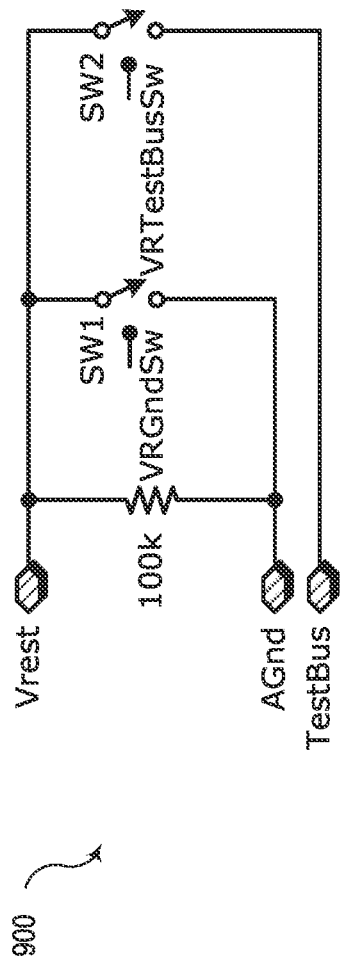
FIG. 9 illustrates a circuit to allow various voltages to be used for exhausting electrodes using a switch matrix for connecting externally supplied voltages or internal voltages to a Vrest (a chosen resting potential between stimulation pulses) circuit node consistent with the present disclosure.

FIG. 9 illustrates a block diagram of a resting potential switch matrix 900 consistent with the present disclosure. The resting potential (Vrest) signal is the resting potential at which all electrodes may equalize their potential before and after stimulation. In some embodiments, the Vrest signal may be connected to an external pin to allow for an externally supplied voltage or for external bypass capacitance and high impedance bias networks between Vrest and the electrodes and may be connected internally for equalization for all channels. The resting potential switch matrix 900 comprises switches SW1 and SW2 that connect the Vrest output to AGnd and TestBus, respectively.

Figure 10:
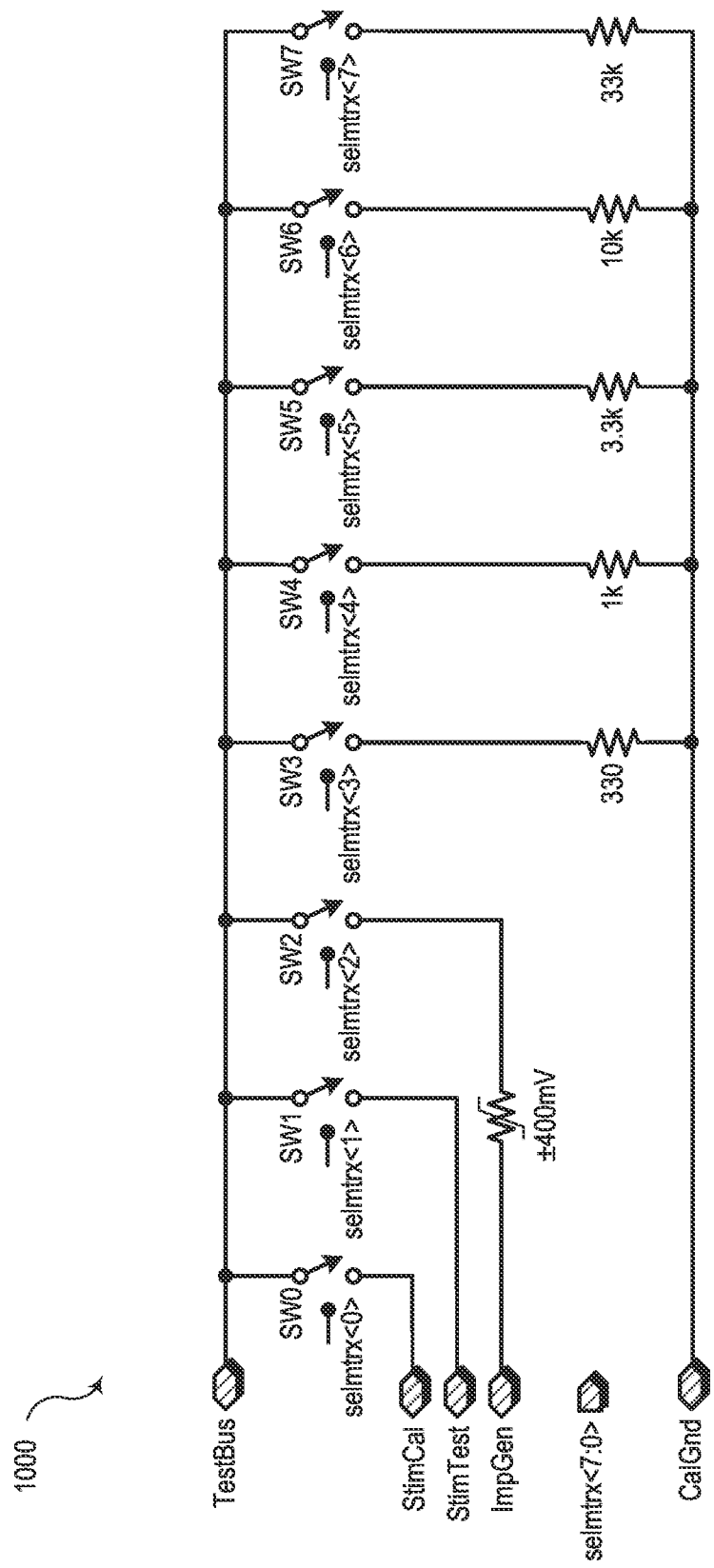
FIG. 10 illustrates a testing circuit to allow testing of stimulation accuracy before connecting to an electrode in contact with excitable tissues, consisting of a switch matrix and defined loads, and also includes an input to connect an external impedance test signal to any one or more of a plurality of channels consistent with the present disclosure.

FIG. 10 illustrates a testing circuit to allow testing of stimulation accuracy before connecting to an electrode in contact with excitable tissues, consisting of a switch matrix and defined loads, and also includes an input to connect an external impedance test signal to any one or more of a plurality of channels consistent with the present disclosure. The test subsystem may provide test functions for measuring individual channel electrode impedances and calibrating channel stimulation current levels. A matrix of selectable impedances may be connected to the TestBus and is used to measure and calibrate individual channel stimulation current levels and stim current matching between different channels. In some embodiments, HV signals are generated using this calibration method so the impedance generation (ImpGen) pad is protected. The test subsystem comprises a switched impedance matrix 1302.

In various embodiments, the test circuit to test stimulation accuracy prior to use of an electrode to stimulate excitable tissues. An external signal used for testing may be applied using the Stim Test input. In various embodiments, the Stim Test input may be connected to an external signal generator. A StimCal input may be used to calibrate an electrode.

FIG. 11 illustrates a circuit diagram of neurostimulation and neurorecording circuit 1100 to isolate an electrode terminal from a recording terminal consistent with embodiments of the present disclosure. A stimulation electrode may connect to the circuit 1100 at the electrode terminal, while a recording circuit connects at the recording terminal. A first transistor 1102 limits the amplitude of the positive voltage relative to its gate voltage and a threshold voltage of the first transistor 1102. A second transistor 1104 limits the amplitude of the negative voltage relative to its gate voltage and a threshold voltage of the second transistor 1104. In the illustrated embodiment, the first transistor 1102 and the second transistor 1104 are embodied as Metal Oxide Semiconductor Field-Effect Transistors (MOSFETs), with the first transistor 1102 being an N-Type Metal Oxide Semiconductor (NMOS) device and the second transistor 1104 being a P-Type Metal Oxide (PMOS) device.

Circuit 1100 is effective at protecting a recording or sensing system connected to the recording terminal, and can provide a low impedance path; however, the design may require a larger size relative to other embodiments that offer similar impedance. A larger device size may introduce difficulties for implantation. Further, a larger size may also introduce larger parasitic capacitances, which can result in more noise in the circuit 1100. Various embodiments discussed herein may reduce the required device size in comparison to circuit 1100.

FIG. 12 illustrates a diagram of a circuit 1200 to isolate neurorecording circuitry from neurostimulation circuitry consistent with embodiments of the present disclosure. Transistors 1202 and 1204 may either create a low-impedance, a medium-impedance, or a high-impedance path from an electrode terminal to a recording terminal (of FIG. 11) based on the mode of operation of circuit 1200. A high-impedance path may be created by causing transistors 1202 and 1204 to operate in a saturation region. Similarly, a low-impedance path may be created by causing transistors 1202 and 1204 to operate in a cutoff region. Finally, a medium-impedance may be created by causing transistors 1202 and 1204 to operate in a triode region, in which the effective impedance is between the low impedance of the saturation region and the high impedance of the cutoff region. Bias currents, Bias N and Bias P, may be provided to transistors 1202 and 1204, respectively.

Circuit 1200 may operate in three primary modes. In a disable mode, circuit 1200 creates a high impedance between the electrode terminal and the recording terminal to prevent the flow of current between the electrode terminal and the recording terminal. The disable mode may be used when the circuit 1200 is not recording. The disable mode may be enabled by reducing the bias currents, Bias N and Bias P, such that transistors 1202 and 1204 operate in a cutoff region.

In a stimulation mode, circuit 1200 creates a static medium impedance between the electrode terminal and the recording terminal, and the recording terminal voltage is limited when a stimulation enable signal is provided. The stimulation mode may provide less overshoot than the active mode, but the reduced overshoot is provided by higher impedance, which increases thermal noise and degrades recording. Stimulation mode may be used when a channel that is being recorded is going to also initiate a stimulation pulse. In some embodiments, the signal to cause circuit 1200 to enter the stimulation mode (i.e., Stimulation Enable N and Stimulation Enable P) may be the same signal used to activate a stimulation current source for the channel. The stimulation mode may be enabled by applying a Stimulation Enable N and a Stimulation Enable P signal to transistors 1206 and 1208, respectively. When Stimulation Enable N is set high, transistor 1216 is bypassed, and transistor 1218 is diode-connected because the gate and the drain of transistor 1218 are electrically connected. In the stimulation mode, the voltage between the electrode terminal and the recording terminal is limited.

In an active mode, circuit 1200 creates a low impedance between the electrode terminal and the recording terminal until a stimulation pulse is detected, at which point circuit 1200 will create a medium impedance state between the electrode terminal and the recording terminal and limit the recording terminal voltage. Circuit 1200 may be configured in the active mode using external control logic. In the illustrated embodiment, the circuit is in active mode when the Stim En N and Stim En P signals are high. When these signals are low, transistors 1206 and 1208 are in the cutoff mode. Transitioning transistors 1206 and 1208 to the active mode bypasses transistors 1216 and 1222, which are controlled by comparators 1210 and 1212, and which effectively bypasses the active mode of the clamp. In one specific embodiment, the control logic may be incorporated into stimulation ASIC 202 illustrated in FIG. 2A or FIG. 2B.

Comparator 1210 may be used to compare a voltage at the electrode terminal to a positive reference value, $+V_{ref}$, and comparator 1212 may be used to compare a voltage at node 1214 to a negative reference value, $-V_{ref}$. When a signal above the positive reference value is not present, an output of comparator 1210 is low, and transistor 1216 operates in the cutoff region. As a result of transistor 1216 operating in the cutoff region, the voltage at the gates of transistors 1202 and 1218 is pulled toward the positive supply voltage, based on the connection to the bias current, Bias N; however, the gate voltage is limited by diodes 1220. In some embodiments, the voltage applied to the gates of transistors 1202 and 1218 may be limited to approximately 4 Volts by diodes 1220. The limited gate voltage may maintain a high power supply rejection ("PSR") and provide a constant impedance across the power supply range. In some embodiments, the power supplies (not shown) may range from +/−4.5V to +/−15V.

Similarly, when a signal below the negative reference value is not present, an output of comparator 1212 is high, and transistor 1222 operates in the cutoff region. As a result of transistor 1222 operating in the cutoff region, the voltage at the gates of transistors 1204 and 1224 is pulled toward the negative supply voltage, based on the connection to the bias current, Bias P; however, the gate voltage is limited by diodes 1226. The gate voltage may be set using diodes 1226. In some embodiments, the voltage applied to the gates of transistors 1202 and 1218 may be limited to approximately 4 Volts by diodes 1226.

The voltage applied at the gates of transistors 1202 and 1218 and 1204 and 1224 may be set by diodes 1220 and 1226, respectively, which may be selected such that transistors 1202 and 1204 operate in the deep triode or linear region in the active mode. Such operation may allow circuit 1200 to be reasonably sized while offering a low resistance and low capacitance, which may improve coupled noise performance. Transistors 1202 and 1204 should provide high PSR because recording and stimulation may take place at the same time using. In various embodiments, system 1200 may provide a high PSR for a channel being used for recording while another channel is being used for stimulation.

When a signal at the electrode terminal above the positive reference voltage, $+V_{ref}$, is present, the output of comparator 1210 becomes high. As a result, the gate voltage of transistor 1216 increases, and transistor 1216 bypasses diodes 1220, which results in a drop in the voltage at the gates of transistors 1202 and 1218. The reduced voltage at the gates of transistors 1202 and 1218 increases the impedance between the electrode terminal and the recording terminal.

Similarly, when a signal below the negative reference voltage, $-V_{ref}$, is present at node 1214, the output of comparator 1212 becomes high. As a result, the gate voltage of transistor 1222 increases, and transistor 1222 bypasses diodes 1226, which results in a drop in the voltage at the gates of transistors 1204 and 1224. The reduced voltage at the gates of transistors 1204 and 1224 increases the impedance between the electrode terminal and the recording terminal.

When a stimulation pulse is initiated, the pulse generates a voltage in the stimulated tissue that is compared to $+V_{ref}$ and $-V_{ref}$ by comparators 1210 and 1212, respectively. If no stimulation pulse is present, the circuit 1200 operates in the active mode because the voltage at the gates of transistors 1202 and 1204 places the transistors in deep triode region of operation. In the deep triode region of operation transistors 1202 and 1204 present a low impedance between the electrode terminal and the recording terminal. When a pulse is detected, circuit 1200 enters the active mode because the operation of comparators 1210 and 1212 reduce the voltage at the gates of transistors 1202 and 1204. The reduced gate voltage increases the resistance of transistors 1202 and 1204. The increased voltage reduces the current flow between the electrode terminal and the recording terminal to prevent damage to sensitive recording equipment connected to the recording terminal.

The components of circuit 1200 may be selected to minimize power utilization. Minimizing power utilization is an important design consideration for embodiments that may be implanted because implanted devices require a power source, such as a battery. In some embodiments, circuit 1200 may operate using 1 uA with a voltage between about 4.5 V and 15 V. Low power consumption may maximize the useable life of an implanted component and provide other benefits. In some embodiments, comparators 1210 and 1212 may utilize energy from a stimulation pulse to improve the response time of circuit 1200 in the active mode to limit the voltage of the signal.

An anti-parallel diode load 1228 is coupled to the recording terminal to reduce the time for transistors 1202 and 1204 to respond to changes. The anti-parallel diode load 1228 may allow current to flow to transistors 1202 and 1204 in response to an overvoltage condition and a transition to a voltage-limited state. In some embodiments, the voltage-limited state may limit the voltage at the recording terminal to a fixed range. In some embodiments the range may be between about ±250 mV and about ±350 mV. Once the circuit enters a steady state, the voltages are less than a threshold voltage draw. Further the power drawn from a stimulation pulse is small (e.g., on the order of 50 nA). Charge balance is still maintained in this state by drawing approximately equivalent current in the positive/negative direction and keeping that current at a minimum.

When circuit 1200 is in active mode and a signal is being recorded, the circuit 1200 may react to limit a voltage generated by a stimulation pulse. In some embodiments, comparators 1210 and 1212 may utilize energy from the stimulation pulse to charge the capacitances of transistors 1202 and 1204 and comparators 1210 and 1212. An anti-parallel diode pair 1228 provides a path to sink current from the initial stimulation pulse and charge the capacitances of the transistors 1202 and 1204 and comparators 1210 and 1212. The use of energy from a stimulation pulse to charge capacitances in circuit 1200 may enable a fast circuit response and allow circuit 1200 to quickly limit a voltage in circuit 1200 caused by a stimulation pulse.

Figure 13:
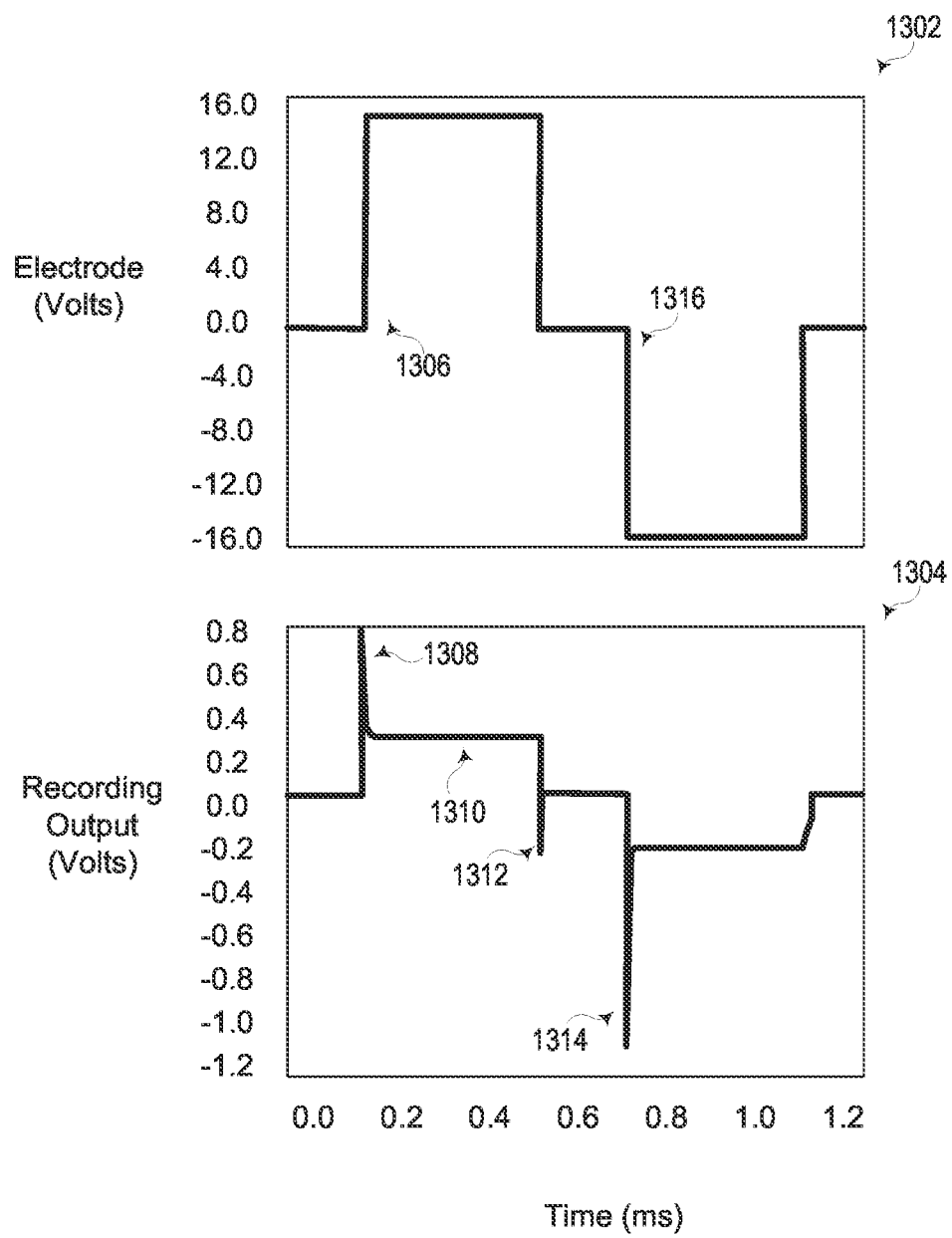
FIG. 13 illustrates a plot over time showing a response of an electrode and recording interface circuit in an active mode consistent with embodiments of the present disclosure.

FIG. 13 illustrates plots over time showing a response of a neurostimulation and neurorecording circuit in an active mode consistent with embodiments of the present disclosure. The neurostimulation and neurorecording circuit may be embodied by circuit 1200 illustrated in FIG. 12. Plot 1302 shows a voltage applied to an electrode terminal connected to a neurostimulation circuit, while plot 1304 shows a voltage at a recording terminal. As illustrated in plot 1302, a first stimulation pulse 1306 drives the voltage to +15V, and a second stimulation pulse 1316 drives the voltage to −15V.

The stimulation pulses shown in plot 1302 create an overvoltage condition shown in plot 1304 that causes the neurostimulation and neurorecording circuit to restrict the voltage at the recording terminal. As the electrode voltage rises, the circuit begins to increase the impedance between the electrode and the recording terminal. The voltage at the recording terminal overshoots 1308 a steady state value due to the sharp rising edge of the stimulation pulse 1306, capacitive coupling, and the response time of the circuit; however, the circuit settles to a steady state 1310 with a recording terminal of approximately +350 mV. When the stimulation pulse subsides, another overshoot 1312 occurs before the recording terminal settles back to 0 Volts.

A falling edge of the second stimulation pulse 1316 may again cause an overshoot 1314 at the recording terminal; however, the voltage at the recording terminal quickly settles at a steady state value for the duration of the second stimulation pulse 1316. The recording terminal returns to 0 Volts when the second stimulation pulse subsides.

Figure 14:
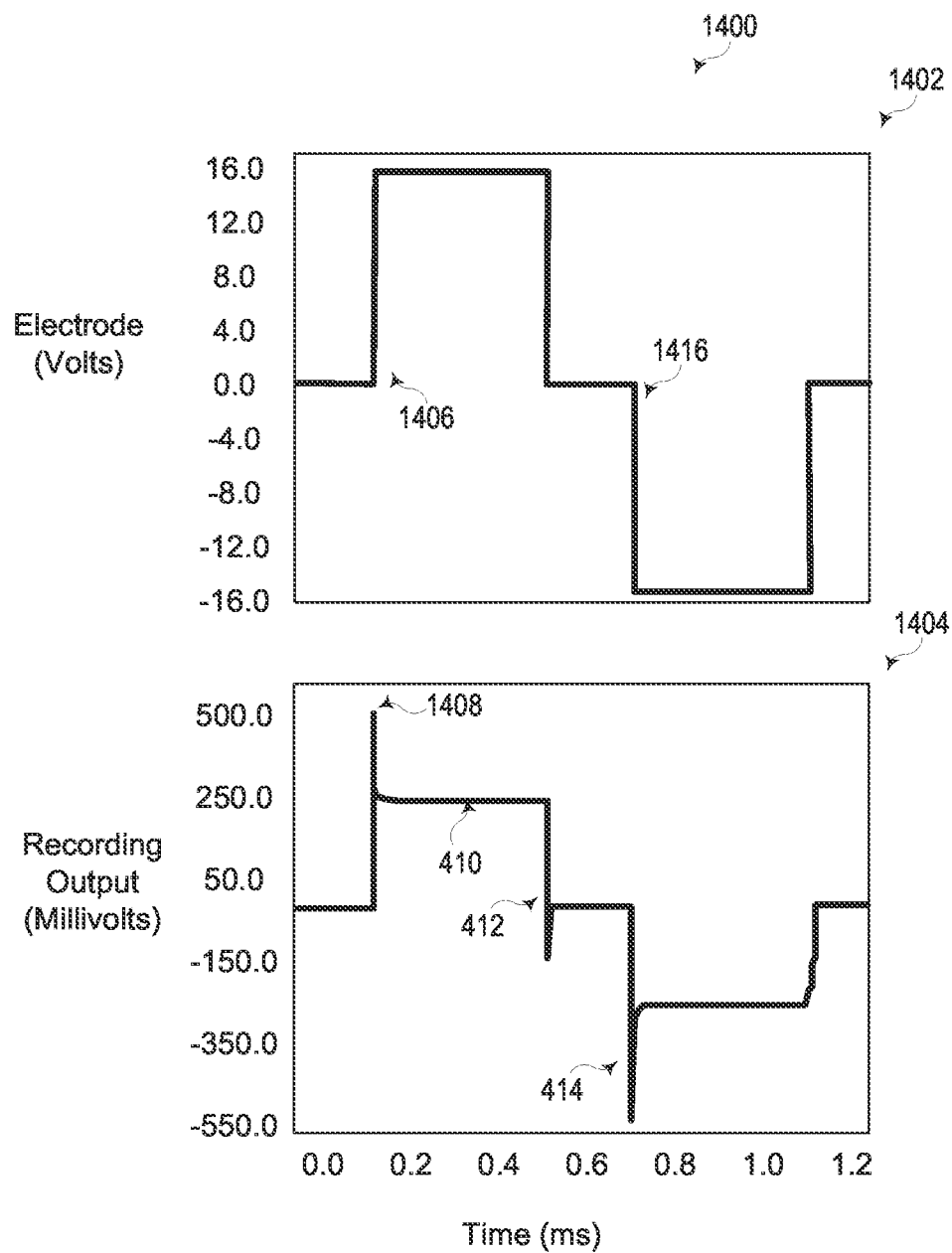
FIG. 14 illustrates a plot over time showing a response of an electrode and recording interface circuit in a stimulation mode consistent with embodiments of the present disclosure.

FIG. 14 illustrates plots 1400 over time showing a response of a neurostimulation and neurorecording circuit in a stimulation mode consistent with embodiments of the present disclosure. In the stimulation mode, the neurostimulation and neurorecording circuit creates a static medium impedance between the electrode and the recording terminal and the recording terminal voltage is limited when a stimulation enable signal is provided.

Like the plot shown in FIG. 13, an overshoot 1408 occurs due to the sharp rising edge of the stimulation pulse 1406, capacitive coupling, and the response time of the circuit; however, the magnitude of the overshoot 1408 is reduced in comparison to the overshoot shown in FIG. 13. The circuit settles to a steady state 1410 with a recording terminal of approximately +250 mV. When the stimulation pulse subsides, another overshoot 1412 occurs, but again, the overshoot is smaller than the corresponding overshoot shown in FIG. 13.

A falling edge of the second stimulation pulse 1416 may again cause an overshoot 1414 at the recording terminal before the voltage at the recording terminal settles at a steady state value for the duration of the second stimulation pulse 1416. The recording terminal returns to 0 Volts when the second stimulation pulse 1416 subsides.

Many changes may be made to the details of the above-described embodiments without departing from the underlying principles of the invention. The scope of the present invention should, therefore, be determined only by the following claims.

What is claimed is:

1. A neurostimulation and neurorecording interface control circuit, comprising:
    a stimulation terminal;
    a recording terminal; and
    an interface control subsystem in electrical communication with the stimulation terminal and the recording terminal and disposed between the stimulation terminal and the recording terminal, the interface control subsystem configured to operate in:
        a disable mode in which the neurostimulation and neurorecording interface control circuit is configured to provide a high impedance between the stimulation terminal and the recording terminal;
        an active mode in which the neurostimulation and neurorecording interface control circuit is configured to provide a low impedance between the stimulation terminal and the recording terminal; and
        a stimulation mode in which the neurostimulation and neurorecording interface control circuit is configured to provide an impedance between the high impedance of the disable mode and the low impedance of the active mode.

2. The neurostimulation and neurorecording interface control circuit of claim 1, wherein the neurostimulation and neurorecording interface control circuit is further configured to detect an overvoltage condition at the stimulation terminal and to reduce a voltage at the recording terminal by transitioning to the disable mode.

3. The neurostimulation and neurorecording interface control circuit of claim 2, wherein the voltage on the recording terminal is limited to about +/−400 mV when the overvoltage condition at the stimulation terminal is present.

4. The neurostimulation and neurorecording interface control circuit of claim 3, further comprising:
    a first comparator to compare a positive reference voltage to a first voltage at an electrode terminal and to activate a first signal if the voltage at the electrode terminal exceeds the positive reference voltage;
    wherein the first signal limits the voltage at the recording terminal.

5. The neurostimulation and neurorecording interface control circuit of claim 4, wherein the interface control subsystem further comprises:
    a first transistor, and
    a second transistor disposed in series between the stimulation terminal and the recording terminal.

6. The neurostimulation and neurorecording interface control circuit of claim 5, further comprising:
    a second comparator to compare a negative reference voltage to a second voltage at a junction between the first transistor and the second transistor and to activate a second signal if the voltage at the junction between the first transistor and the second transistor is below the negative reference voltage;
    wherein the second signal limits a voltage at the recording terminal.

7. The neurostimulation and neurorecording interface control circuit of claim 6, wherein the first comparator and the second comparator are configured to detect a voltage in tissue generated by a stimulation pulse and to cause the neurostimulation and neurorecording interface control circuit to transition from the active mode to the stimulation mode in response to the stimulation pulse.

8. The neurostimulation and neurorecording interface control circuit of claim 5, further comprising a first series of diodes configured to set a voltage at a gate of the first transistor and configured to generate a high Power Supply Rejection to limit noise in biopotential recordings.

9. The neurostimulation and neurorecording interface control circuit of claim 5, wherein the first transistor and the second transistor operate in a saturation region in the active mode and operate in a cutoff region in the disable mode.

10. The neurostimulation and neurorecording interface control circuit of claim 5, wherein the first transistor and the second transistor operate in a triode region in the stimulation mode.

11. The neurostimulation and neurorecording interface control circuit of claim 4, further comprising an anti-parallel diode coupled to the recording terminal.

12. The neurostimulation and neurorecordinq interface control circuit of claim 1, wherein the low impedance between the stimulation terminal and the recording terminal measures less than 200 Ohms.

13. A neurostimulation and neurorecording system, comprising:
an electrode array to transduce biopotential signals and to stimulate excitable tissue;
a stimulator and recorder component in electrical communication with the electrode array, comprising:
a stimulation subsystem in electrical communication with at least one electrode in the electrode array which generates a stimulation signal to stimulate excitable tissue in proximity to the at least one electrode;
a recording subsystem in electrical communication with a protected output of a stimulation ASIC to allow a measurement of a biopotential signal from the at least one electrode protected by an electrical circuit protection subsystem; and
an interface control subsystem comprising:
a stimulation terminal in electrical communication with the stimulation subsystem, and
a recording terminal in electrical communication with the recording subsystem;
wherein the interface control subsystem is configured to present a low impedance path between the stimulation terminal and the recording terminal when the stimulation signal is not present and to present a high impedance path between the stimulation terminal and the recording terminal when the stimulation signal is present.

14. The neurostimulation and neurorecording system of claim 13, wherein the interface control subsystem is further configured to present the high impedance path between the stimulation terminal and the recording terminal in response to an overvoltage condition and to reduce a voltage at the recording terminal.

15. The neurostimulation and neurorecording system of claim 14, wherein the voltage on the recording terminal is limited to about +/−400 mV when the overvoltage condition at the stimulation terminal is present.

16. The neurostimulation and neurorecording system of claim 13, further comprising an electrode switch matrix in electrical communication with the stimulation subsystem and comprising a plurality of impedances that may be selected to adjust a recovery time post-stimulation to exhaust a residual charge.

17. The neurostimulation and neurorecording system of claim 13, further comprising a window comparator to determine whether a voltage applied to at least one electrode in the electrode array is outside a defined voltage window established by a maximum threshold and a minimum threshold to detect stimulation or leakage currents.

18. The neurostimulation and neurorecording system of claim 13, further comprising a rail comparator to determine whether a voltage of the stimulation signal and applied to the at least one electrode in the electrode array is within a threshold value of one of a positive voltage rail or a negative voltage rail.

19. The neurostimulation and neurorecording system of claim 13, wherein the interface control subsystem further comprises:
a first transistor, and
a second transistor disposed in series between the stimulation terminal and the recording terminal.

20. The neurostimulation and neurorecording system of claim 13 further comprising a test circuit to test stimulation accuracy prior to use of an electrode to stimulate excitable tissues.

21. The neurostimulation and neurorecording system of claim 20, wherein the test circuit consists of a switch matrix comprising a plurality of loads.

22. The neurostimulation and neurorecording system of claim 13, further comprising an input to connect to an external impedance test signal to any one or more of a plurality of channels.

23. The neurostimulation and neurorecording system of claim 13, further comprising a watchdog circuit to monitor a system clock signal and output a reset signal to shut down stimulation or disconnect the electrode array upon detection of the system clock signal stopping.

* * * * *